US007727288B2

(12) United States Patent
Nguyen et al.

(10) Patent No.: US 7,727,288 B2
(45) **Date of Patent: *Jun. 1, 2010**

(54) PROCESS FOR STYLING DYED HAIR AND INHIBITING ITS COLOR LOSS DURING SHAMPOOING

(75) Inventors: Nghi Van Nguyen, Edison, NJ (US); David W. Cannell, Plainfield, NJ (US); Cynthia Chong Espino, Princeton, NJ (US); Sawa Hashimoto, Westfield, NJ (US)

(73) Assignee: L'Oreal (FR)

( * ) Notice: Subject to any disclaimer, the term of this patent is extended or adjusted under 35 U.S.C. 154(b) by 498 days.

This patent is subject to a terminal disclaimer.

(21) Appl. No.: 11/280,058

(22) Filed: Nov. 16, 2005

(65) Prior Publication Data

US 2007/0107141 A1 May 17, 2007

(51) Int. Cl.
*D06P 5/02* (2006.01)
*A61Q 5/00* (2006.01)
*A61Q 5/10* (2006.01)

(52) U.S. Cl. ........................... 8/442; 132/202; 132/208; 424/70.1

(58) Field of Classification Search ..................... 8/405, 8/442; 132/202, 208; 424/70.1
See application file for complete search history.

(56) References Cited

U.S. PATENT DOCUMENTS 5,070,171 A 12/1991 O'Lenick, Jr.
5,093,452 A 3/1992 O'Lenick, Jr.
5,149,765 A 9/1992 O'Lenick, Jr.
5,248,783 A 9/1993 O'Lenick
5,739,371 A 4/1998 O'Lenick, Jr.
6,451,747 B1 * 9/2002 Decoster ..................... 510/119
6,482,400 B1 11/2002 Collin et al.
6,685,926 B2 2/2004 Hehner et al.
2003/0165453 A1 * 9/2003 Nguyen et al. ........... 424/70.12
2004/0062737 A1 4/2004 Nguyen et al.
2004/0063592 A1 4/2004 Nguyen et al.
2004/0241114 A1 * 12/2004 Gupta ......................... 424/61
2006/0286057 A1 12/2006 Cannell et al.
2007/0110691 A1 5/2007 Nguyen et al.

FOREIGN PATENT DOCUMENTS

DE 197 35 865 4/1999
EP 1 238 648 9/2002
EP 1 302 195 4/2003
EP 1 312 341 5/2003
EP 1402881 A1 * 3/2004
EP 1 733 717 12/2006
WO 93/25179 12/1993

OTHER PUBLICATIONS

CTFA International Cosmetic Ingredient Dictionary and Handbook, 8th ed. vol. 2, 2000, pp. 1701-1703.

* cited by examiner

*Primary Examiner*—Eisa B Elhilo
(74) *Attorney, Agent, or Firm*—Lerner, David, Littenberg, Krumholz & Mentlik, LLP

(57) ABSTRACT

A process for styling dyed hair fibers in a manner which inhibits subsequent color loss during shampooing involving contacting the dyed hair fibers with a composition containing: (a) at least one polyamine compound having at least two amino groups; (b) at least one anionic silicone; (c) at least one film-forming polymer; and (d) optionally, at least one surfactant, and wherein (a) is present in the composition in an amount sufficient to inhibit color loss during shampooing.

12 Claims, No Drawings

PROCESS FOR STYLING DYED HAIR AND INHIBITING ITS COLOR LOSS DURING SHAMPOOING

BACKGROUND OF THE INVENTION

The present invention relates to a process for styling dyed hair fibers in a manner which inhibits subsequent color loss during shampooing. The process involves contacting the dyed hair fibers with a composition containing at least one polyamine compound having at least two amino groups, at least one anionic silicone, and at least one film-forming polymer.

There are essentially two dyeing methods used for imparting color onto hair fibers: “permanent” dyeing and “semi-permanent” dyeing.

The first, also known as oxidation dyeing, uses “oxidation” dye precursors, which are colorless or weakly colored compounds. Once mixed with oxidizing products, at the time of use, these precursors lead to colored compounds and dyes via a process of oxidative condensation. In this case, the colorations obtained are generally very colorfast and strong.

The second, also known as direct dyeing, uses direct dyes, which are nonionic or ionic dyes and colored compounds capable of producing a more or less pronounced change of the natural color of the hair, resistant to shampoo-washing several times. These dyes may or may not be used in the presence of an oxidizing agent.

In contrast with oxidation dye precursors, a direct dye is a relatively voluminous molecule that does not penetrate easily into the core of the fiber. Consequently, even though considerable progress has been made in this field, the phenomenon of bleeding of the coloration during shampooing is still non-negligible, even if the dye(s) used is (are) chosen from cationic species. Moreover, the use of certain cationic direct dyes may be reflected by a reduction in the working qualities of the shampoos used after coloration, especially as regards the duration of the lather.

Fixing the hairstyle is an important element in hair styling, and involves maintaining a shape that has already been carried out, or simultaneously shaping and fixing the hair.

In accordance with the invention, the term “hair styling composition” relates to any kind of hair composition that can be used to affect hair styling. The most prevalent hair styling compositions on the cosmetic market for shaping and/or maintaining the hairstyle are spray compositions containing a solvent, usually alcohol- or water-based, and one or more materials, generally polymer resins. One of the functions of polymer resins is to form links between the hairs, these materials also being called fixatives, in a mixture with various cosmetic adjuvants. This solution is generally packaged either in an appropriate aerosol container, which is pressurized with the aid of a propellant, or in a pump flask.

Some other known hair styling compositions include styling gels and mousses, which are generally applied to the wetted hair before brushing or setting it. In contrast to the conventional aerosol lacquers, some types of these other known hair styling compositions disadvantageously are not designed to allow the hair to be fixed in a shape created before their application. In fact, these compositions are essentially aqueous and their application wets the hair; hence these compositions are not designed to maintain the initial shape of the hairstyle. In order to shape and fix the hairstyle, therefore, it is necessary to carry out subsequent brushing and/or drying with these types of compositions.

The polymers contained in these types of hair styling compositions affix themselves not only to the hair fibers themselves, but also to dyes present thereon. Consequently, when the dyed hair is shampooed, both the polymers and some of the dye itself are washed from the hair.

Thus, it is an object of the present invention is to provide a process for styling dyed hair in a manner which reduces the degree of color loss during shampooing.

SUMMARY OF THE INVENTION

In order to achieve these and other advantages, the present invention is drawn to a process for styling dyed hair fibers in a manner which inhibits subsequent color loss during shampooing, involving contacting the dyed hair fibers with a composition containing:

(a) at least one polyamine compound having at least two amino groups;

(b) at least one anionic silicone;

(c) at least one film-forming polymer; and (d) optionally, at least one surfactant, and wherein (a) is present in an amount sufficient to inhibit dyed hair fibers which have been styled from losing their color during shampooing.

DETAILED DESCRIPTION

Other than in the operating examples, or where otherwise indicated, all numbers expressing quantities of ingredients and/or reaction conditions are to be understood as being modified in all instances by the term “about”.

“Amino groups” as defined herein includes primary amino groups, secondary amino groups, and tertiary amino groups, and further includes amino groups which are terminal, pendant, and intercalated in a skeleton of the at least one polyamine compound, but does not, for example, include quaternary amino groups, amido groups, imino groups, nitrilo groups, or heteroatom analogs of any of the foregoing.

“At least one” as used herein means one or more and thus includes individual components as well as mixtures/combinations.

The at least one polyamine compound of the present invention comprises at least two amino groups, preferably at least three amino groups, more preferably at least four amino groups, more preferably at least five amino groups, more preferably at least six amino groups, more preferably at least seven amino groups, more preferably at least eight amino groups, more preferably at least nine amino groups, and more preferably at least ten amino groups.

In one embodiment of the present invention, the at least one polyamine compound may, for example, be chosen from aminated polysaccharides comprising at least two amino groups, such as, for example, hydrolysates of aminated polysaccharides comprising greater than two amino groups. In one embodiment, the at least one polyamine compound may, for example, be chosen from polymers. Suitable polymers for use as the at least one amine compound are polymers comprising at least two amino groups as defined herein. Non-limiting examples of suitable polymers include homopolymers comprising at least two amino groups, copolymers comprising at least two amino groups, and terpolymers comprising at least two amino groups. Thus, the at least one polyamine compound comprising at least two amino groups may be chosen from, for example, polymers comprising at least two amino groups formed from (i) at least one monomer unit comprising at least one amino group as defined herein, and, optionally, (ii) at least one additional monomer unit different from the at least one monomer (i); and polymers comprising at least two amino groups formed from (i) at least one monomer comprising at least two amino groups as defined herein, and, optionally, (ii) at least one additional monomer unit different from the at least one monomer (i). According to the present invention, the at least one additional monomer different from the at least one monomer (i) may or may not comprise at least one amino group as defined herein. A particularly preferred polyamine polymer is chitosan.

In one embodiment of the present invention, the at least one polyamine compound is chosen from polyamines. As used herein, "polyamines" comprise at least two repeating units, wherein each unit comprises at least one amino group as defined herein. In one embodiment, polyamines are chosen from polyethyleneimines. Polyethyleneimines suitable for use in the compositions of the present invention may optionally be substituted. Non-limiting examples of polyethyleneimines which may be used in the composition according to the present invention are the Lupasol™ products commercially available from BASF. Suitable examples of Lupasol™ polyethyleneimines include Lupasol™ PS, Lupasol PL, Lupasol™ PR8515, Lupasol™ G20, Lupasol™ G35 as well as Lupasol™ SC® Polythyleneimine Reaction Products (such as Lupasol™ SC-61B®, Lupasol™ SC-62J®, and Lupasol™ SC-86X®). Other non-limiting examples of polyethyleneimines which may be used in the composition according to the present invention are the Epomin™ products commercially available from Aceto. Suitable examples of Epomin™ polyethyleneimines include Epomin™ SP-006, Epomin™ SP-012, Epomin™ SP-018, and Epomin™ P-1000.

Polyamines suitable for use in the present invention may also be chosen from polyvinylamines. Examples thereof include Lupamines® 9095, 9030, 9010, 5095, 1595 from BASF.

The polyamine compounds can also be substituted. An example of such a compound is PEG-15 Cocopolyamine from Cognis.

In another embodiment, the at least one polyamine compound comprising at least two amino groups is chosen from proteins and protein derivatives. Non-limiting examples of suitable proteins and protein derivatives for use in the present invention include those listed at pages 1701 to 1703 of the C.T.F.A. International Cosmetic Ingredient Dictionary and Handbook, $8^{th}$ edition, vol. 2, (2000). In one embodiment, the at least one polyamine compound comprising at least two amino groups is chosen from wheat protein, soy protein, oat protein, collagen, and keratin protein.

In one embodiment, the at least one polyamine compound comprising at least two amino groups is not chosen from proteins and protein derivatives. In one embodiment, the at least one polyamine compound comprising at least two amino groups is not chosen from compounds comprising lysine, compounds comprising arginine, and compounds comprising histidine. In one embodiment, the at least one polyamine compound comprising at least two amino groups is chosen from compounds comprising lysine, compounds comprising arginine, compounds comprising histidine, and compounds comprising hydroxylysine.

In the present invention, the at least one polyamine compound is employed in an amount sufficient to inhibit color bleeding from hair fibers during shampooing. Typically, it may be employed in an amount of from greater than 0% to 30% by weight, preferably from 5% to 20% by weight, and more preferably from 5% to 10% by weight, based on the weight of the composition as a whole. In general, non-limiting examples of anionic silicones which may be used in the present invention include silicone carboxylates, silicone phosphates, silicone sulfates, silicone sulfosuccinates, and silicone sulfonates.

Suitable silicone carboxylates may be chosen from water soluble silicone compounds comprising at least one carboxylic acid group, oil soluble silicone compounds comprising at least one carboxylic acid group, water-dispersible silicone compounds comprising at least one carboxylic acid group, and silicone compounds comprising at least one carboxylic acid group which are soluble in organic solvents. In one embodiment, the at least one silicone compound comprising at least one carboxylic acid group further comprises at least one alkoxylated chain, wherein the at least one alkoxy group may be chosen from terminal alkoxy groups, pendant alkoxy groups, and alkoxy groups which are intercalated in the skeleton of the at least one silicone compound. Non-limiting examples of at least one alkoxy group include ethylene oxide groups and propylene oxide groups.

The at least one carboxylic acid group may be chosen from terminal carboxylic acid groups and pendant carboxylic acid groups. Further, the at least one carboxylic acid may be chosen from carboxylic acid groups in free acid form, i.e., —COOH, and carboxylic acid groups in salt form, i.e., —COOM, wherein M may be chosen from inorganic cations, such as, for example, potassium cations and sodium cations, and organic cations.

In one embodiment, the at least one silicone compound comprising at least one carboxylic acid group is chosen from silicone compounds of formula (I) and salts thereof:

(I)

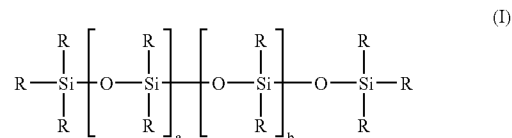

wherein: a is an integer ranging from 1 to 100; b is an integer ranging from 0 to 500; R, which may be identical or different, are each chosen from optionally substituted hydrocarbon groups comprising from 1 to 9 carbon atoms, optionally substituted phenyl groups, and groups of formula (II):

(II)

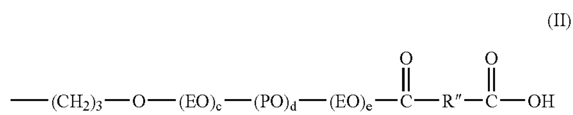

wherein: c, d, and e, which may be identical or different, are each integers ranging from 0 to 20; EO is an ethylene oxide group; PO is a propylene oxide group; and R" is chosen from optionally substituted divalent hydrocarbons, such as alkylene groups and alkenylene groups comprising from 2 to 22 carbon atoms, and optionally substituted divalent aromatic groups, such as groups of formula (III):

(III)

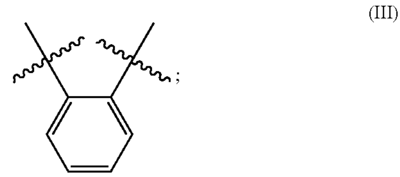

and groups of formula (IV):

(IV)

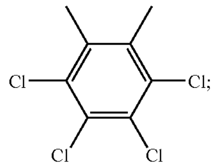

with the proviso that at least one of the R groups is chosen from groups of formula (II) and with the further proviso that when only one of the R groups is chosen from groups of formula (II), the other R groups are not all methyl groups.

Non-limiting examples of the at least one silicone compound include those commercially available from Noveon under the name Ultrasil® CA-1 Silicone and Ultrasil® CA-2 Silicone, both of which correspond to formula (V) below. This silicone carboxylate is sold in the free acid form as an emulsifier and dispersing aid for complexing fatty cationic amines and quaternary amines. Thus, in one embodiment, the at least one silicone compound is chosen from silicone compounds of formula (V) and salts thereof:

(V)

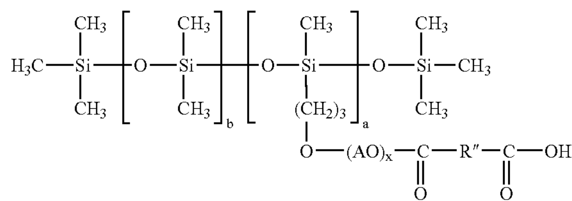

wherein: a is an integer ranging from 1 to 100; b is an integer ranging from 0 to 500; AO is chosen from groups of formula (VI):

$$-(EO)_c—(PO)_d-(EO)_e— \quad (VI)$$

wherein: c, d, and e, which may be identical or different, are each integers ranging from 0 to 20; EO is an ethylene oxide group; and PO is a propylene oxide group; x is an integer ranging from 0 to 60; R" is chosen from optionally substituted divalent hydrocarbons, such as alkylene groups and alkenylene groups comprising from 2 to 22 carbon atoms, and optionally substituted divalent aromatic groups, such as groups of formula (III):

(III)

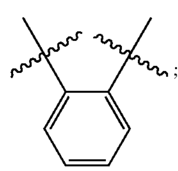

and groups of formula (IV):

(IV)

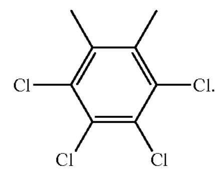

Non-limiting examples of the at least one silicone compound include those described in U.S. Pat. Nos. 5,248,783 and 5,739,371, the disclosures of which are incorporated herein by reference, and which are silicone compounds of formula (I).

Suitable silicone phosphates may be chosen from water-soluble silicone compounds comprising at least one phosphate group, oil soluble silicone compounds comprising at least one phosphate group, water-dispersible silicone compounds comprising at least one phosphate group, and silicone compounds comprising at least one phosphate group which are soluble in organic solvents.

In one embodiment, the at least one silicone compound comprising at least one phosphate group further comprises at least one alkoxylated chain, wherein the at least one alkoxy group may be chosen from terminal alkoxy groups, pendant alkoxy groups, and alkoxy groups which are intercalated in the skeleton of the at least one silicone compound. Non-limiting examples of at least one alkoxy group include ethylene oxide groups ("EO"=$—CH_2—CH_2—O—$) and propylene oxide groups ("PO"=$C_3H_6O$).

The at least one phosphate group may be chosen from terminal phosphate groups and pendant phosphate groups. Further, the at least one phosphate group may be chosen from groups of formula $—O—P(O)(OH)_2$, groups of formula $—O—P(O)(OH)(OR)$, and groups of formula $—O—P(O)(OR)_2$, wherein R may be chosen from H, inorganic cations, and organic cations. Non-limiting examples of inorganic cations include alkali metals, such as, for example, potassium lithium, and sodium. A non-limiting example of organic cations is at least one additional silicone compound which may be identical to or different from the at least one silicone compound bonded to the other oxygen of the phosphate group.

In one embodiment, the at least one silicone compound comprising at least one phosphate group is chosen from silicone compounds of formula (I):

$$O{=}P(OR^1)_3. \quad (I)$$

wherein $R^1$, which may be identical or different, are each chosen from H, organic cations, inorganic cations, optionally substituted hydrocarbons (such as alkyl groups and alkenyl groups comprising from 1 to 22 carbon atoms), optionally substituted aromatic groups; groups of formula (II) and salts thereof:

$$CH_3(CH_2)_x—O-(EO)_c—(PO)_d-(EO)_e—CH_2CH_2— \quad (II)$$

wherein: c, and d, which may be identical or different, are each integers ranging from 0 to 20; e is an integer ranging from 0 to 19; and x is an integer ranging from 0 to 21; groups of formula (III) and salts thereof:

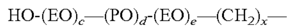
(III)

wherein: c, d, and e, which may be identical or different, are each integers ranging from 0 to 20; and x is an integer ranging from 0 to 21; and groups of formula (IV) and salts thereof:

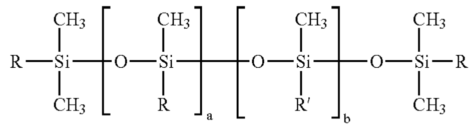
(IV)

wherein: a is an integer ranging from 0 to 200; b is an integer ranging from 0 to 200; R', which may be identical or different, are each chosen from optionally substituted hydrocarbons, such as alkyl groups and alkenyl groups comprising from 1 to 22 carbon atoms, optionally substituted aromatic groups, groups of formula (III) as defined above and salts thereof; and R, which may be identical or different, are each chosen from optionally substituted hydrocarbons, such as alkyl groups and alkenyl groups comprising from 1 to 22 carbon atoms, optionally substituted aromatic groups, optionally substituted divalent hydrocarbons, such as alkylene groups and alkenylene groups comprising from 1 to 22 carbon atoms, optionally substituted divalent aromatic groups, groups of formula (III) as defined above and salts thereof, and groups of formula (V):

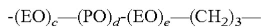
(V)

wherein:

the $(CH_2)_3$ end is bonded to the silicon of the compound of formula (IV) and the (EO) or (PO) end, if present, is bonded to the oxygen of the compound of formula (I); c, d, and e, which may be identical or different, are each integers ranging from 0 to 20; EO is an ethylene oxide group; and PO is a propylene oxide group; and with the proviso that at least one R is chosen from groups of formula (V) and salts thereof; and with the further proviso that at least one $R^1$ is chosen from groups of formula (IV) and salts thereof and at least one other $R^1$ is chosen from H, organic cations, and inorganic cations.

Non-limiting examples of the inorganic cations include alkali metals, such as potassium, lithium, and sodium. Non-limiting examples of the at least one silicone compound include those commercially available from Phoenix Chemical, Inc. of New Jersey under the name of Pecosil®, such as Pecosil® PS-100, Pecosil® PS-112, Pecosil® PS-150, Pecosil® PS-200, Pecosil® WDS-100, Pecosil® WDS-200, Pecosil® PS-100 B, and Pecosil® PS-100 K and those commercially available from Siltech under the name Silphos A-100 and Silphos A-150. Other non-limiting examples of the at least one silicone compound include those described in U.S. Pat. Nos. 5,070,171, 5,093,452, and 5,149,765 the disclosures of which are incorporated herein by reference.

Suitable silicone sulfates for use in the present invention include those represented by formula VI:

(VI)
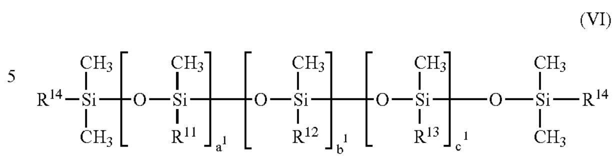

wherein $R^{11}$ is selected from lower alkyl having one to eight carbon atoms or phenyl, $R^{12}$ is $—(CH_2)_3—O-(EO)_x—(PO)_y-(EO)_z—SO_3^{31}-M^+$ wherein M is a cation and is selected from Na, K, Li, or $NH_4$; x, y and z are integers independently ranging from 0 to 100; $R^{13}$ is $—(CH_2)_3—O-(EO)_x—(PO)_y-(EO)_z—H$; $R^{14}$ is methyl or hydroxyl; $a^1$ and $c^1$ are independently integers ranging from 0 to 50; $b^1$ is an integer ranging from 1 to 50. An example thereof is Ultrasil SA-1 silicone commercially available from Noveon.

Suitable silicone sulfosuccinates which may be employed include, but are not limited to, those corresponding to formula VII:

(VII)
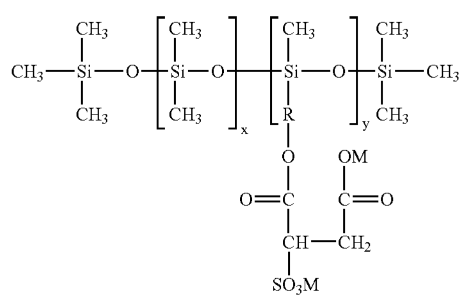

wherein R represents a divalent radical selected from

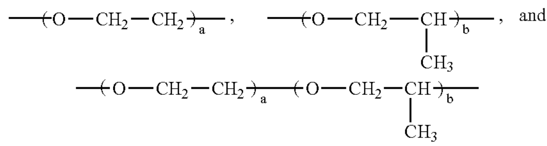

wherein a' and b' range from 0 to 30; x and y are such that the molecular weight ranges from 700 to 1600, and M is an alkali metal such as sodium or potassium, or an ammonium group.

A particularly preferred anionic silicone is Dimethicone PEG-8 phosphate, commercially available from Noveon under the tradename Ultrasil PE-100.

The anionic silicone will be employed in an amount sufficient to inhibit hair from frizzing upon exposure to humidity. Typically, it may be employed in an amount ranging from greater than 0 to 50% by weight, preferably from 5 to 30% by weight, and more preferably from 5 to 15% by weight, based on the weight of the composition as a whole.

Film-forming polymers useful herein are neutralized, non-neutralized or partially neutralized, polymers and resins, wherein the polymers and resins include but are not limited to those containing carboxyl moieties, such as acrylates and other carboxy polymers.

The following are examples of film forming polymers that can be employed by the present invention. The list is not intended to be limiting:

AMPHOMER LV-71 from National Starch (octylacrylamide/acrylates/butylaminoethyl methacrylate copolymer), OMNIREZ-2000 from ISP (PVM/MA half ethyl ester copolymer), RESYN 28-2930 from National Starch (Vinyl acetate/crotonates/vinyl neodecanoate copolymer), LUVIMER 100P from BASF (t-butyl acrylate/ethyl acrylate/methacrylic acid), and ULTRAHOLD STRONG from BASF (acrylic acid/ethyl acrylate/t-butyl acrylamide).

Unneutralized or partially neutralized water-insoluble latexes can also be used as invention film-forming polymers. Included are the following latexes:

AMERHOLD DR-25 from Amerchol (acrylic acid/methacrylic acid/acrylates/methacrylates), LUVIMER 36D from BASF (ethyl acrylate/t-butyl acrylate/methacrylic acid), and ACUDYNE 258 from Rohm & Haas (acrylic acid/methacrylic acid/acrylates/methacrylates/hydroxy ester acrylates).

The film forming polymer may be employed in an amount sufficient to impart and/or maintain a shape on the hair. Typically, it will be employed in an amount of from greater than 0 to 30% by weight, preferably from 1 to 10% by weight, and more preferably from 1 to 5% by weight, based on total weight of composition.

Surfactants

It may be desirable, in certain circumstances, to employ a surfactant such as, for example, a nonionic surfactant, an anionic surfactant, an amphoteric/zwitterionic surfactant, and a cationic surfactant.

Suitable nonionic surfactants are any suitable nonionic surfactants that have an HLB of from about 3 to about 14. The abbreviation "HLB" stands for hydrophilic lipophilic balance. Examples of suitable nonionic surfactants include, but are not limited to, fatty acid esters and alkoxylated, particularly ethoxylated, fatty acid esters of polyhydric alcohols such as glycerols and sorbitol, for example, polyoxyethylene monolaurate, polyoxyethylene monooleate, polyoxyethylene monostearate, sorbitan monolaurate, sorbitan trioleate, generally with a degree of ethoxylation of from about 20 to about 85; mono- and di-alkanolamides, such as the N-acyl derivatives of mono- and di-ethanol amines, and polyethoxylated monoalkanolamides; amine oxides, such as cocoamidopropyl dimethylamine oxides, coco bis-2-hydroxyethyl amine oxides and lauryl dimmethylamine oxide; ethoxylated alkanolamides; ethoxylated oils and fats such as ethoxylated lanolins; and ethoxylated alkylphenols, such as Nonoxynol.

Suitable anionic surfactants include, for example, the following: the alkali metal, ammonium, or amine salts of alkyl sulfates, alkyl ether sulfates, linear alpha-olefin sulfonates, dialkyl sulfosuccinates, alkylamidosulfosuccinates, and alkyl taurates each having from about $C_{12}$ to $C_{18}$ alkyl or alkenyl groups. Particularly preferred are the salts of lauryl sulfates and lauryl ether sulfates the latter having an average level of ethoxylation of 1-3.

Amphoteric/zwitterionic surfactants belong to the category of surface active chemicals that possess a positive and a negative charge in the same molecule and behave as a cation or an anion depending on the pH of the medium. In general, the positive charge is located on a nitrogen atom while the negative charge is carried by a carboxyl or sulfonate group.

There are a large number of amphoteric surfactants that are suitable for use in this invention. They include, for example, lauryl betaine, lauroamphoglycinate, lauroamphopropylsulfonate, lauroamphopropionate, lauroamphocarboxyglycinate, lauryl sultane, myristamidopropyl betaine, myristyl betaine, myristoamphoglycinate, myristyl propionate, stearoamphoglycinate, stearoamphopropionate, stearoamphopropylsulfonate, stearyl betaine, cocamidoethyl betaine, cocamidopropyl betaine, cocamidopropyl hydroxysultane, cocamidopropyl dimethylamine propionate, cocoamphoglycinate, cocoamphocarboxypropionate, cocoamphocarboxyglycinate, coco-betaine, cocoamphopropionate, cocoamphopropylsulfonate.

The amphoteric surfactants presently preferred for use in this invention are: cocamidopropyl betaine, coco-betaine, stearyl betaine, cocoamphocarboxyglycinate, cocoamphodipropionate, and stearoamphoglycinate.

The surfactant may typically be employed in an amount of from greater than 0% by weight to 80% by weight, based on the weight of the composition.

Conditioning agents may also be employed in order to impart added conditioning benefits to the composition. The conditioning agents useful in the present invention are those which are dispersible in water and typically may be chosen from cationic surfactants, silicone compounds, polyalkylene glycols and mixtures thereof, preferably mono long-chain ammonium compounds, hydrophilically substituted cationic surfactants, hydrophilically substituted silicone compounds, polyalkylene glycols, and mixtures thereof.

The type of conditioning agent selected depends on the desired characteristics of the product. Highly water soluble conditioning agents are typically used. A combination of conditioning agents is preferably used to provide benefits provided by the different conditioning agents. Conditioning agents which are less water soluble can be used in combination with highly water soluble conditioning agents.

Cationic surfactants may be used as conditioning agents herein. Suitable cationic surfactants useful herein include, but are not limited to, those generally described as mono long-chain ammonium compounds. Nonlimiting examples of such cationic surfactants include: cetyl trimethyl ammonium chloride available, for example, with tradename CA-2350 from Nikko Chemicals and CTAC 30KC available from KCI, stearyl trimethyl ammonium chloride with tradename Arquad 18/50 available from Akzo Nobel, hydrogenated tallow alkyl trimethyl ammonium chloride, stearyl dimethyl benzyl ammonium chloride, stearyl propyleneglycol phosphate dimethyl ammonium chloride, stearoyl amidopropyl dimethyl benzyl ammonium chloride, stearoyl amidopropyl dimethyl (myristylacetate) ammonium chloride, and N-(stearoyl colamino formyl methy) pyridinium chloride.

Also preferred are hydrophilically substituted cationic surfactants in which at least one of the substituents contain one or more aromatic, ether, ester, amido, or amino moieties present as substituents or as linkages in the radical chain. Nonlimiting examples of hydrophilically substituted cationic surfactants useful in the present invention include the materials having the following CTFA designations: quaternium-16, quaternium-26, quaternium-27, quaternium-30, quaternium-33, quaternium-43, quaternium-52, quaternium-53, quaternium-56, quaternium-60, quaternium-61, quaternium-62, quaternium-70, quaternium-71, quaternium-72, quaternium-75, quaternium-76 hydrolyzed collagen, quaternium-77, quaternium-78, quaternium-79 hydrolyzed collagen, quaternium-79 hydrolyzed keratin, quaternium-79 hydrolyzed milk protein, quaternium-79 hydrolyzed silk, quaternium-79 hydrolyzed soy protein, and quaternium-79 hydrolyzed wheat protein, quaternium-80, quaternium-81, quaternium-82, quaternium-83, quaternium-84, and mixtures thereof.

Highly preferred hydrophilically substituted cationic surfactants include dialkylamido ethyl hydroxyethylmonium salt, dialkylamidoethyl dimonium salt, dialkyloyl ethyl hydroxyethylmonium salt, dialkyloyl ethyldimonium salt, alkyl amidopropyl trimonium salt, polyoxyethylene alkyl ammonium salt, and mixtures thereof; for example, commercially available under the following tradenames; VARISOFT 110, VARISOFT PATC, VARIQUAT K1215 and 638 from Witco Chemical, ETHOQUAD 18/25, ETHOQUAD O/12PG, ETHOQUAD C/25, and ETHOQUAD S/25 from Akzo, DEHYQUART SP from Cognis, and MONAQUAT ISEIS, and MONAQUAT SL-5 available from Uniqema.

The polyalkylene glycols useful herein as conditioning agents include those which are soluble or dispersible in water. Polyethylene glycols are preferred.

Polyalkylene glycols having a molecular weight of more than about 100 are useful herein. Ethylene oxide polymers are preferred in view of their generally good water solubility, dispersibility, and transparency. Polyethylene-polypropylene glycols and polyoxyethylene-polyoxypropylene copolymer polymers having good dispersibility and transparency may also be useful. Suitable anionic surfactants include, for example, the following: the alkali metal, ammonium, or amine salts of alkyl sulfates, alkyl ether sulfates, linear alpha-olefin sulfonates, dialkyl sulfosuccinates, alkylamidosulfosuccinates, and alkyl taurates each having from about $C_{12}$ to $C_{18}$ alkyl or alkenyl groups. Particularly preferred are the salts of lauryl sulfates and lauryl ether sulfates the latter having an average level of ethoxylation of 1-3.

The composition of the present invention may also contain additives, for instance those chosen from the non-exhaustive list such as reducing agents, antioxidants, sequestering agents, softeners, antifoams, moisturizers, emollients, basifying agents, plasticizers, sunscreens, direct dyes or oxidation dyes, pigments, mineral fillers, clays, colloidal minerals, nacres, nacreous agents, fragrances, peptizers, preserving agents, fixing or non-fixing polymers, proteins, vitamins, antidandruff agents, aliphatic or aromatic alcohols, and more particularly ethanol, benzyl alcohol, modified or unmodified polyols, such as glycerol, glycol, propylene glycol, dipropylene glycol, butylene glycol or butyl diglycol, volatile silicones, mineral, organic or plant oils, oxyethylenated or non-oxyethylenated waxes, paraffins, fatty acids, associative or non-associative thickening polymers, fatty amides, fatty esters, fatty alcohols, and the like.

The composition according to the invention may be vaporizable, for example by a pump, or may be a pressurized aerosol composition. It may be vaporizable by a dispensing valve controlled by a dispensing head, which in turn comprises a nozzle, which vaporizes the aerosol composition. A vaporizable composition according to the invention comprises an appropriate solvent. Advantageously, the appropriate solvent comprises at least one solvent chosen from water and lower alcohols. In accordance with the invention, the term lower alcohol means a $C_1$ to $C_4$ aliphatic alcohol, such as ethanol. When the vaporizable composition according to the invention is an aerosol composition, it additionally comprises an appropriate amount of propellant. The propellant comprises compressed or liquefied gases, which are normally employed for the preparation of aerosol compositions. Suitable gases include compressed air, carbon dioxide, nitrogen, and gases, which may be soluble in the composition, such as dimethyl ether, fluorinated or non-fluorinated hydrocarbons, and mixtures thereof.

The present invention additionally provides an aerosol device comprising a vessel comprising an aerosol composition, which comprises a liquid phase (or juice) comprising at least one hair styling material, as described above, in an appropriate medium and a propellant, and a dispenser, such as a dispensing valve, for dispensing said aerosol composition from the vessel.

The present invention provides for the dyed hair fibers to be treated before, during, or after the shaping of the hairstyle.

The present invention will be better understood from the examples which follow, all of which are intended for illustrative purposes only and are not meant to unduly limit the scope of the invention in any way.

EXAMPLES

Example 1

Effectiveness of Polyamine/Anionic Silicone/Film Former Solutions as Leave on Treatments Bleached hair swatches were dyed with Redken HiFusion R, with application duration of 30 minutes and rinsed with water for 1 minute. Then 1 g of the polyamine/anionic silicone/film former mixture per gram of hair was applied to the colored swatches, distributed thoroughly throughout the swatch, then the swatch was blow-dried until completely dry. A total of five swatches were tested for each treatment. The initial L value of the hair swatches was then taken. The L value indicates lightness/darkness of the color being read. The higher number indicates lighter color. The treated hair swatches were shampooed with 0.5 g of 10% SLES solution (pH 6.27)/g hair for 30 seconds then rinsed for 10 seconds under running water. This was repeated for a total of 6 shampoos. The hair was then blow-dried, and the final L value was taken. The change in L value was calculated. The higher in the change in L the more color loss after shampooing.

The following polyamine/anionic silicone/film former solutions were used:

| | A | B | C | D |
|---|---|---|---|---|
| Polyethyleneimine | — | 2 | — | 4 |
| Ultrasil PE-100 | — | 0.5 | — | 0.5 |
| Amphomer LV-71 (neutralized to 100% with AMP) | 6 | 6 | — | — |
| PVP K-90 | — | — | 5 | 5 |
| Water | | qs to 100 | | |

The result is as follows in Table 1 which shows that after six shampoos, hair swatches treated with the mixtures containing PEI and Ultrasil PE-100 had better color retention than the ones treated with the mixtures without PEI and Ultrasil PE-100.

TABLE 1

Change in L Value after 6 shampoos

| Treatment | Change in L Value |
|---|---|
| A | 33.32 |
| B | 26.30 |
| C | 30.64 |
| D | 23.28 |

Example 2

Effectiveness of Shampoo Containing Polyamine/Anionic Silicone/Film Former

Bleached hair swatches were dyed with Redken HiFusion R, with application duration of 30 minutes and rinsed with water for 1 minute. The colored swatch was blow-dried and the initial L value of the hair swatches was then taken. The L value indicates lightness/darkness of the color being read. The higher number indicates lighter color. The hair swatches were treated with the shampoo (0.5 g of shampoo/g hair) for 30 seconds then rinsed for 10 seconds under running water. This was repeated for a total of 10 shampoos. After 3 shampoos, 6 shampoos and 10 shampoos, the treated hair swatches were blow-dried, and the final L value was taken. The change in L value was calculated. The higher in the change in L the more color loss after shampooing.

The following polyamine/anionic silicone/film former shampoo were used:

| | E | F |
|---|---|---|
| Polyethyleneimine | 2 | — |
| Ultrasil PE-100 | 0.5 | — |
| Amphomer LV-71 (neutralized to 100% with AMP) | 1 | — |
| SLES | 7.6 | 7.6 |
| Mackam 2CSF 40 CG | 30 | 30 |
| Water | qs to 100 | |

The result is as follows in Table 2 which shows that after 3, 6, 10 shampoos, the shampoo containing Amphomer LV-71, PEI, and Ultrasil imparts better color retention than the shampoo without Amphomer LV-71, PEI, and Ultrasil.

TABLE 2

| | Change in L Value after 3, 6, and 10 shampoos | | |
|---|---|---|---|
| Treatment | 3 × shampooed | 6 × shampooed | 10 × shampooed |
| E | 4.64 | 9.33 | 24.52 |
| F | 5.49 | 12.31 | 28.35 |

What is claimed is:

1. A process for styling dyed hair fibers in a manner which inhibits subsequent color loss during shampooing comprising contacting the dyed hair fibers with a composition containing:

(a) at least one polyamine compound having at least two amino groups;

(b) at least one anionic silicone;

(c) at least one film-forming polymer; and (d) optionally, at least one surfactant, and wherein (a) is present in the composition in an amount sufficient to inhibit color loss during shampooing.

2. The process of claim 1 wherein (a) is a polyethyleneimine.

3. The process of claim 1 wherein (a) is a polyvinylamine.

4. The process of claim 1 wherein (a) is a chitosan.

5. The process of claim 1 wherein (a) is present in the composition in an amount up to about 30% by weight, based on the weight of the composition.

6. The process of claim 1 wherein (a) is present in the composition in an amount of from about 5 to about 10% by weight, based on the weight of the composition.

7. The process of claim 1 wherein (b) is a silicone phosphate.

8. The process of claim 1 wherein (b) is present in the composition in an amount up to about 50% by weight, based on the weight of the composition.

9. The process of claim 1 wherein (b) is present in the composition in an amount of from about 5 to about 15% by weight, based on the weight of the composition.

10. The process of claim 1 wherein (c) is present in the composition in an amount up to about 30% by weight, based on the weight of the composition.

11. The process of claim 1 wherein (c) is present in the composition in an amount of from about 1 to about 5% by weight, based on the weight of the composition.

12. The process of claim 1 wherein the composition is a hair styling or curl retaining product.

* * * * *